United States Patent [19]

Alexander et al.

[11] Patent Number: 5,731,450

[45] Date of Patent: Mar. 24, 1998

[54] OIL ADDUCT CONDITIONERS

[75] Inventors: Anatoly Alexander, Berkeley Heights; Ratan K. Chaudhuri, Lincoln Park, both of N.J.

[73] Assignee: ISP Van Dyk Inc., Belleville, N.J.

[21] Appl. No.: 544,750

[22] Filed: Oct. 18, 1995

[51] Int. Cl.$^6$ .............................. C07C 53/00; A61K 7/48
[52] U.S. Cl. ........................ 554/221; 554/213; 554/214; 554/219; 554/227; 554/122; 554/126; 560/116; 560/118; 560/127; 560/128; 424/401; 424/70.1
[58] Field of Search .................... 424/401, 70.1; 554/122, 126, 213, 214, 219, 221, 227; 560/116, 118, 127, 128; 252/857

[56] References Cited

U.S. PATENT DOCUMENTS 4,196,134  4/1980  Ball et al. .............................. 260/404.8

Primary Examiner—Jyothsan Venkat
Attorney, Agent, or Firm—Marilyn J. Maue; Walter Katz; Joshua J. Ward

[57] ABSTRACT

This invention relates to the synthesis of vegetable and synthetic oil adducts and to the adduct products having the formula $$[R]_aCH_2-OR_1$$
$$|$$
$$[CH-OR_2]_b$$
$$|$$
$$[CH_2-OR_3]_c.$$

14 Claims, 1 Drawing Sheet

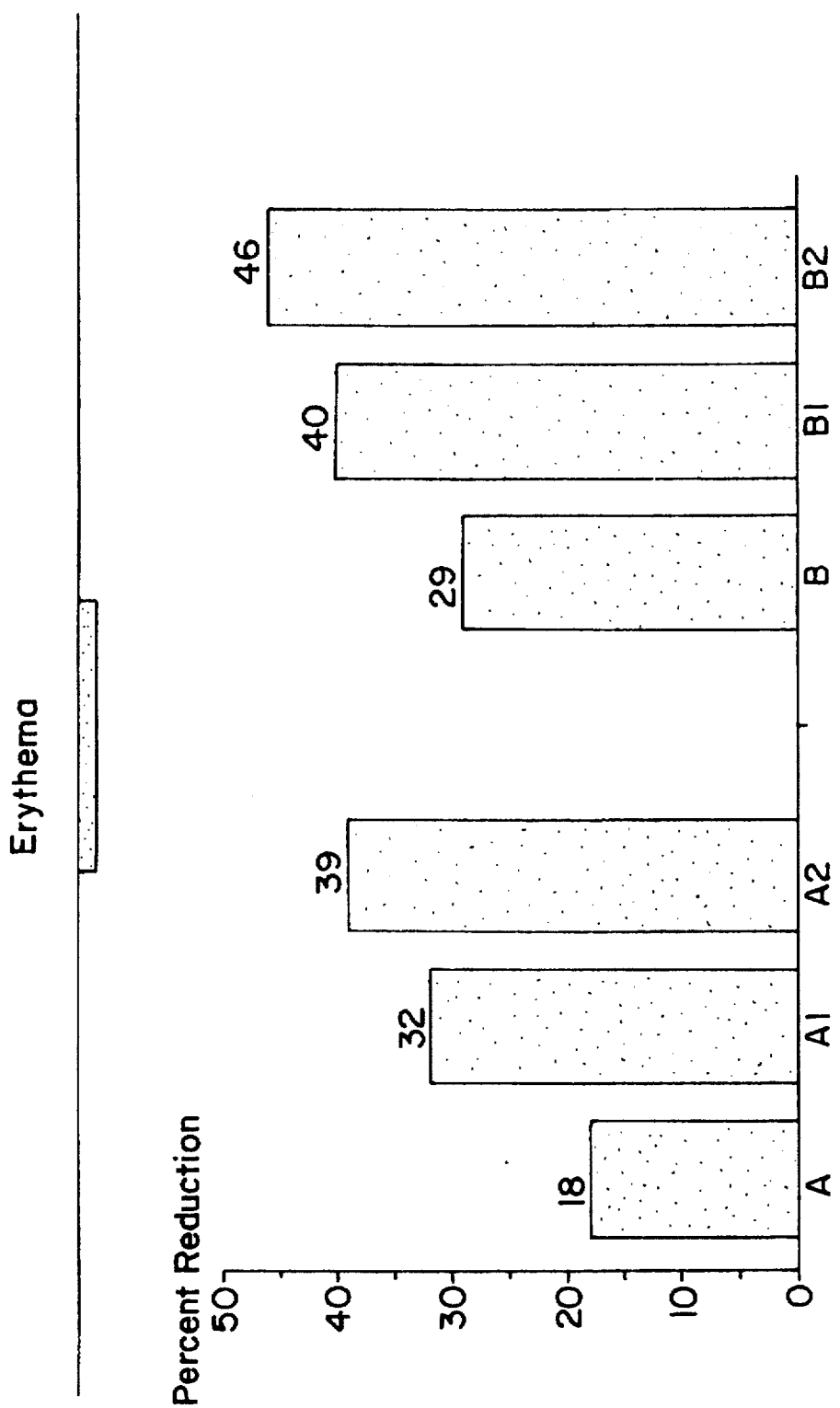

OIL ADDUCT CONDITIONERS

DESCRIPTION OF THE PRIOR ART

Human skin is made up of several cellular layers which coat and protect the keratin and collagen fiber proteins that form the skeleton of its structure. The outermost of these layers, referred to as the stratum corneum, is composed of 250Å protein bundles surrounded by 80Å thick layers. Hair similarly has a protective outer coating enclosing the hair fiber or cuticle. The surface of the cuticle is covered with a thin layer, namely the epicuticle, which contains lipids and protein. Anionic surfactants can penetrate the stratum corneum membrane and the cuticle and, by delipidization, can destroy the membrane integrity. This interference with the skin and hair protective membranes causes skin roughness as well as eye irritation and may eventually lead to interaction of the surfactant with keratin and hair proteins causing erythema, reduction of barrier protection and loss of water retention.

Central heating, air-conditioning, rapid climatic changes, increasing exposure to air pollution and frequent use of hair treatment products, also contribute to skin and hair damage. Thus, the main concern of the cosmetologist is to counteract these deleterious influences on skin and hair and to support or augment the natural skin and hair functions. Ideal cosmetic preparations, Such as lotions, creams etc., should provide replacement of skin surface lipids removed due to the surfactant or solvent action. Unfortunately, emollient additives presently employed in creams and lotions do not provide the desired skin softening persistency. On the other hand, cosmetic cleansers ideally should cleanse without defatting and/or drying the hair and skin and without irritating the ocular mucosae or leaving skin taut after frequent use. However, most lathering soaps, shower and bath products, shampoos and soap bars fail in this respect.

The literature concerning the Diels-Alder reaction of dienophiles and fatty acids, their esters or oils is complex and overlapping as illustrated in U.S. Pat. Nos. 4,196,134 and 4,740,367 which describe the use of vegetable oil polycarboxylated adducts for personal care applications. Although these adducts have been employed as emollients in creams and lotions, they are tacky and possess such high viscosities that their formulations require the addition of complex surfactant mixtures to achieve the degree of lubricity needed for spreadability and uniform application. Examples of such formulations are disclosed in European Patent Publication WO 92/06669.

Other shortcomings of the polycarboxylated adducts is their skin irritating effects which necessarily limits their concentration in formulations for personal care to less than 20% of the composition. Further, because of the high viscosity of these polycarboxylated adducts, only about 30 mole % of acid functionality can be incorporated in the adduct product. This low level of incorporation results in a high concentration of conjugated olefin in the oil adduct which is susceptible to rancidity due to auto-oxidation. However, it has been postulated that the acid functionality is critical in providing the structural conformation that allows the hydrophilic group to remain at the polar interface of the epidermal lipids bilayer thereby contributing the skin conditioning effect at low humidity [D. S. Osborne, Cosmetics & Toiletries, 103, page 57 (1988)].

Thus, it is the aim of research to discover non-tacky fatty ester adducts of significantly lower viscosity and irritability which retain moisturizing effects over extended periods of use. Accordingly, it is an object of this invention to provide such improved adducts which not only retain the beneficial properties of the prior glyceride adducts but additionally and unexpectedly display superior substrate substantivity and markedly lower viscosity thus providing valuable non-greasy, non-tacky hair and skin conditioning agents having a low acid number per molecule and which are capable of forming an invisible barrier as protection against alkali or acid induced erythema.

Another object of this invention is to provide an economical and commercially feasible method for synthesizing the unique adducts herein described.

These and other objects of the invention will become apparent from the following disclosure.

THE INVENTION

In accordance with this invention there is provided an oil adduct of a conjugated polyolefinic mono-, di- or tri- ester of a polyhydric or monohydric alcohol having the formula

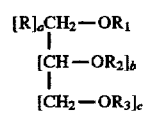

wherein b and c are each independently 0 or 1;

a is zero when b and/or c has a positive value and a is one when b and c are zero;

R is hydrogen or $C_1$ to $C_{20}$ alkyl;

$R_1$, $R_2$ and $R_3$ are each independently —$COR_6$, or

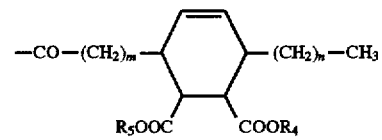

in which $R_6$ is $C_{10}$ to $C_{22}$ alkenyl or alkyl optionally substituted with hydroxy, m and n each have a value of from 3 to 9 with the proviso at least one of $R_1$, $R_2$ and $R_3$ in the adduct product is

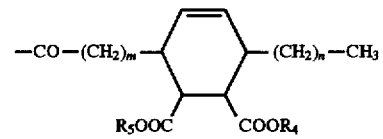

at least one of $R_4$ and $R_5$ is a $C_1$ to $C_{22}$ radical of alkyl, alkenyl or hydroxy alkyl and any other of $R_4$ or $R_5$ is hydrogen or a $C_1$ to $C_{22}$ radical of alkyl, alkenyl or hydroxy alkyl.

The oils from which the above adducts are derived contain linoleic and linolenic and/or ricinoleic acids as found in certain vegetable oils which contain the functional group

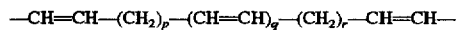

wherein p and r each independently have a value of 0 to 3 and q has a value of 0 or 1. Such natural vegetable oils include dehydrated castor oil and almond, apricot kernel, candelnut, corn, cottonseed, grapefruit seed, hempseed, kapok, linseed, oiticica, olive, orangeseed, palm, peanut, perilla, popyseed, rice bran, safflower, sesame, soybean, sunflowerseed, teaseed, tung wood, walnut and wheat germ oils wherein polyunsaturated sites are conjugated in the presence of between about 0.05 and about 2 wt. % of an isomerization catalyst such as iodine, sulfur, sulfur dioxide, sodium, nickel, selenium and the like, when subjected to a temperature of from about 80° C. to about 250° C., as described for example in U.S. Pat. No. 4,196,134, incorporated herein by reference. Synthetic glycerine, propylene or ethylene glycol fatty oils having conjugated double bonds include mono-, di- and tri-linoleates, and the like.

Of the above oils, the triglycerides containing a major amount of linoleic acid, such as soybean, sunflower, and safflower oils, are preferred, soybean oil, being most preferred.

The present adduct product are obtained by the Dieis-Alder condensation reaction between a conjugated polyolefinic oil including synthetic oils and vegetable oils as in mono-, di- or tri-glycerides of linoleic, linolenic and/or resinoic acids containing the functional group $—CH=CH—(CH_2)_p—(CH=CH)_q—(CH_2)_r—CH=CH—$, and a coreactant ester of the formula $R_5OOC—CH=CH—COOR_4$.

The conjugation of the fatty oil can be carried out as a first step in a staged reaction followed by Dieis-Alder condensation at from about 150° C. to about 260° C. with the $R_5OOC—CH=CH—COOR_4$ coreactant. However, the process in which the conjugation and condensation reactions are carried out simultaneously in a single stage is preferred. The molar ratio of $—CH=CH—CH=CH—$ radical to ester coreactant is between about 1:1 and about 3:1.

Generally, the reactions are effected over a period of from about 0.5 to about 15 hours with gentle mixing at atmospheric or slightly elevated pressure. The adduct product is recovered after stripping off low molecular weight by-products, e.g. by fractional or vacuum distillation, and collecting a clear oil product having a Brookfield viscosity of between about 100 and about 1500 cps. The most preferred product of this invention is the mono(2-ethyl hexyl) maleate/soybean oil adduct (MSO); although any of the low odor oil adducts are also recommended.

The present products retain all of the beneficial properties of the adducts disclosed in U.S. Pat. No. 4,740,367 and European Patent Publication WO 92/06669, also incorporated herein by reference. However in addition, the adducts of this invention are non-tacky and, notwithstanding their significantly higher molecular weight, possess a viscosity reduced by at least 25% over the patented adducts. Further, the low acid number of the low viscosity adduct, permits high loading, up to 80%, in personal care and other formulations without objectionable skin irritation. The present adducts are suitably employed as oil or water based emulsions, dispersions or colloids for moisturizing and conditioning effects in personal care formulations as well as in leather and vinyl treating compositions. For example, treating vinyl upholstery or car roofs with compositions containing high concentrations of the present adduct extends the life of the plastic and protects it against scratching, cracking and dulling.

Generally, the effective concentration of the present adduct in commercial personal care formulations is between about 0.1 and about 30 wt. %, preferable between about 0.5 and about 15 wt. %, based on total composition; whereas with leather and vinyl treating compositions, the adduct concentration can be as high as 50% of the composition. These compositions can be in the form of a solution or a lotion, cream or salve as an emulsion, suspension, dispersion, colloid and the like. The incorporation of the present adduct into these commercial products not only provides superior moisturizing but also acts as a barrier to skin and leather penetrants, e.g. methyl nicotinate, and other irritating or surface dulling substances.

By way of illustration, the FIGURE compares the reduction of skin erythema caused by 0.85% methyl nicotinate in water based gel in the absence of a maleated adduct (Sample A), in the presence of 10 wt. % maleic acid-soybean oil adduct (Sample A1) and in the presence of 10 wt. % MSO (Sample A2) and that caused by 1% methyl nicotinate in a rice oil based gel in the absence of a maleated adduct (Sample B), in the presence of 8 wt. % maleic acid-soybean oil adduct (Sample B1) and in the presence of 8 wt. % MSO (Sample B2). As shown, almost a two fold reduction in nicotinate irritation is realized in the water solution containing 10% maleic acid adduct and an additional 7% is achieved with the same amount of the present adduct and almost 40% reduction is obtained in the oil composition containing 8 wt. % of the maleic acid-soybean oil adduct and an additional 6% improvement is obtained using 8% of the present MSO adduct.

The formulations containing the present adducts additionally may contain up to 10 wt. % surfactant and surfactant mixtures. Suitable surfactants include anionic, amphoteric, non-ionic and cationic surfactants which can be used individually or in mixtures, e.g. such mixtures as are disclosed in European Patent Publication WO 92/06669. Preferred surfactants, when employed, include anionic and non-ionic surface active agents and mixtures thereof.

Adduct formulations may also contain a fragrance, preservative, additional emollients, film-forming polymers, Vitamin E and the like.

Generally the preservative can be employed in a concentration of between about 0 and about 20 wt. %, preferably between about 0.2 and about 10 wt. %, based on total composition. The remaining additives are present in individual amounts ranging between about 0 and about 15 wt. % depending on the option of the consumer.

The following represent formulations which typify the use of the present adducts.

| Ingredients | % W/W |
| --- | --- |
| CONDITIONING SOAP BAR | |
| Bradpride Soap Base | 97.00 |
| MSO | 1.00 |
| Fragrance | 2.00 |
| CONDITIONING NAIL POLISH REMOVER | |
| Acetone (99%) | 90.00 |
| MSO | 10.00 |
| AFTER SHAVE BALM | |
| Phase A | |
| Deionized water | 52.5 |
| Crosslinked polyacrylic acid (Carbomer 941) | 25.00 |
| Phase B | |
| triethanolamine (99%) | 0.50 |
| Ethanol (40% anhydrous) | 10.00 |
| Phase C | |
| MSO | 5.00 |
| 20 Ethoxylated stearate (CERASYNT ® 840) | 3.00 |
| Mineral Oil/lanolin Alcohol | 3.50 |

| Ingredients | % W/W |
|---|---|
| Phase D | |
| Propylene Glycol/diazolidinyl urea/methyl and propyl paraben (GERMABEN ® II) | 0.50 |
| Fragrance | q.s. |
| | 100.00 |

This composition was prepared by the above order of addition A–C under constant agitation at 75°80° C. then cooling to 40° C. before adding D and gradually cooling to room temperature.

| SUNSCREEN | |
|---|---|
| INGREDIENTS | % W/W |
| Phase A | |
| Octyl dimethyl p-aminobenzoic acid (ESCALOL ® 507) | 8.00 |
| Octyl methoxycinnamate (ESCALOL ® 557) | 7.50 |
| Benzophenone-3 (ESCALOL ® 567) | 5.00 |
| Brij 72 (Steareth-2) | 2.00 |
| Arlacel 83 (Sorbitan Sesquioleate) | 1.00 |
| Octyl Palmitate (CERAPHYL ® 368) | 5.00 |
| Phase B | |
| Water, deionized | q.s. |
| Propylene glycol | 4.00 |
| Carbopol 1342 (Acrylic Acid polymer) | 0.20 |
| Methylparaben | 0.20 |
| Propylparaben | 0.20 |
| Phase C | |
| Triethanolamine 99% | 0.20 |
| Phase D | |
| Imidazolidinyl Urea (GERMALL ® 115) | 0.15 |
| Phase E | |
| Fragrance | 0.20 |
| Phase F | |
| MSO | 3.00 |
| | 100.00% |

Preparation Procedure
1. Disperse the carbopol and prepare Phase B.
2. Heat Phase A and Phase B to 80° C.
3. Add Phase A to Phase B at 80° C. and mix for 30 minutes.
4. Add Phase C at 80° C. and mix it thoroughly. Cool to 35° C., mix Phase D and Phase E into it. Add Phase F.
5. Cool to room temperature, homogenize and package.

| AFTER SUN MOISTURE LOTION | |
|---|---|
| INGREDIENTS | % W/W |
| Phase A | |
| Cocoa butter | 1.00 |
| Isostearyl neopentanoate | 5.00 |
| Mineral oil | 7.00 |
| Tocopheryl acetate (Vitamin E acetate) | 0.50 |
| PEG-40 stearate (Myrj 52S) | 1.00 |
| Petrolatum (Penreco Super) | 2.00 |
| Paraffin 130/135 | 2.00 |
| Avocado Oil | 0.50 |

| AFTER SUN MOISTURE LOTION | |
|---|---|
| INGREDIENTS | % W/W |
| Phase B | |
| Acrylic Acid Copolymer (Carbomer 1342) | 0.40 |
| MSO | 3.00 |
| Phase C | |
| Water, deionized | q.s. |
| Glycerin | 5.00 |
| Methylparaben | 0.20 |
| Propylparaben | 0.20 |
| Aloe Vera Gel (Veragel Liquid 1:1) | 10.00 |
| Phase D | |
| Triethanolamine 99% | 0.40 |
| Phase E | |
| Imidazolidinyl Urea (GERMALL ® 115) | 0.15 |
| Phase F | |
| Fragrance | 0.20 |
| | 100.00% |

Preparation Procedure
1. Combine Phase C and heat to 80° C.
2. Disperse MSO into Carbomer 1342 and prepare Phase B.
3. Add Phase B to Phase C at 80° C. and mix for 15 minutes.
4. Combine and heat Phase A to 80° C.
5. Add Phase A to Phase BC at 80° C. Mix for 15 minutes. Add Phase D to it and mix thoroughly.
6. Cool to 35° C. and add Phase E and F to it. Cool to room temperature and package.

| MOISTURIZING WATER RESISTANT SUNSCREEN GEL | |
|---|---|
| INGREDIENTS | % W/W |
| Phase A | |
| Water, deionized | q.s. |
| Methyl vinyl ether/maleic anhydride Decadiene crosslinked polymer (STABILEZE ® 06) | 0.40 |
| Phase B | |
| Sodium Hydroxymethylglycinate (SUTTOCIDE ® A) | 0.40 |
| Phase C | |
| Phenoxyethanol | 0.60 |
| Phase D | |
| MSO | 2.00 |
| Aloe Vera Gel (10X concentrate) | 0.20 |
| Tocopheryl acetate | 0.05 |
| Soluble collagen | 0.05 |
| Octyl methoxycinnamate (ESCALOL ® 557) or Octyl Dimethyl PABA (ESCALOL ® 507) | 5.00 |
| Fragrance | 0.10 |
| | 100.00% |

Preparation Procedure
1. Heat Phase A to 80° C. to 85° C. Mix until uniform.
2. Lower temperature to 60° C. Add Phase B.
3. Mix thoroughly, being careful not to aerate the batch.
4. Add Phase C.
5. Add Phase D one ingredient at a time in order listed. Mix well between additions.

DRY OIL BODY SPRAY

| INGREDIENTS | % W/W |
| --- | --- |
| Phase A | |
| Dioctyl malate (CERAPHYL ® 45) | 20.10 |
| MSO | 8.00 |
| Octyl dimethyl PABA (ESCALOL ® 507) | 1.40 |
| Fragrance | 0.50 |
| Cyclomethicone (siloxane) | 45.00 |
| Alcohol SD 40 (ethanol) | 25.00 |
| | 100.00% |

Preparation Procedure

1. In a suitable vessel weight ingredients in order listed with agitation.
2. Mix until uniform and package.

BATH OIL

| INGREDIENTS | % W/W |
| --- | --- |
| Phase A | |
| Tridecyl neopentanoate (CERAPHYL ® 55) | 20.00 |
| ($C_{12}$–$C_{15}$) alkyl lactate (CERAPHYL ® 41) | 5.00 |
| Isopropyl myristate | 15.00 |
| PEG-40 Sorbitan Peroleate (Arlatone T) | 2.00 |
| Mineral oil 65/75 | 53.00 |
| MSO | 5.00 |
| Fragrance and Preservative | q.s. |
| | 100.00% |

Preparation Procedure

In a suitable vessel able to contain the entire batch, weigh all ingredients, mix until uniform and package.

MULTI-PROTECTION BROAD SPECTRUM MOISTURIZER

| INGREDIENTS | % W/W |
| --- | --- |
| Phase A | |
| Cetyl alcohol | 1.00 |
| Cyclomethicone (siloxane SWS-03314) | 2.00 |
| Cetearyl alcohol and Ceteareth-20 (Promulgen D) | 4.00 |
| Tridecyl neopentanoate (CERAPHYL ® 55) | 6.00 |
| Octyl methoxycinnamate (ESCALOL ® 557) | 6.00 |
| Benzophenone-3 (ESCALOL ® 567) | 3.00 |
| Steareth-21 (Brij 721) | 1.50 |
| Steareth-2 (Brij 72) | 1.00 |
| Tocopheryl acetate (Vitamin E acetate) | 0.50 |
| Phase B | |
| Water, deionized | 55.35 |
| Crosslinked polyacrylic acid (Carbopol 934) | 0.20 |
| Glycerin | 5.00 |
| Methylparaben | 0.20 |
| Propylparaben | 0.20 |
| Aloe Vera Gel (Veragel liquid 1:1) | 10.00 |
| Phase C | |
| Sodium hydroxide 10% aq. soln. | 0.70 |
| Phase D | |
| Imidazolidinyl urea (GERMALL ® 115) | 0.15 |
| Phase E | |
| Fragrance | 0.20 |

MULTI-PROTECTION BROAD SPECTRUM MOISTURIZER

| INGREDIENTS | % W/W |
| --- | --- |
| Phase F | |
| MSO | 3.00 |
| | 100.00% |

Preparation Procedure

1. Disperse the Carbopol into the water, and then combine the other ingredients to prepare Phase B.
2. Heat Phase A and Phase B to 80° C.
3. Add Phase A to Phase B and mix thoroughly.
4. Add Phase C to Phase AB. Mix at 80° C. for 15 minutes.
5. Cool to 35° C. and add Phase D and E. Add Phase F. Cool to room temperature and package.

Other formulations suitable for the ester adducts of this invention include Examples 10, 11 and 12 of U.S. Pat. No. 4,740,367 wherein the present esterified adduct is substituted for PCW-178. This patent disclosure is incorporated herein by reference.

Having thus described the invention reference is now had to the Examples which set forth methods of synthesizing preferred adducts. However, these examples are not to be construed as limiting to the scope of this invention as more broadly defined above and in the appended claims.

EXAMPLE 1

Into a stainless 1 liter autoclave was charged 104 g mono(2-ethylhexyl)maleate and 329 g soybean oil and the mixture was sparged with nitrogen for 10 minutes at ambient temperature, after which 1.3 g of elemental iodine was added and the autoclave was again sparged with nitrogen for an additional 5 minutes. The contents of the autoclave was stirred at a rate of 890 rpm and the autoclave was sealed and heated to 225° C. over a period of 2 hours and held at that temperature for 30 minutes. The autoclave was then cooled to room temperature and the contents discharged and passed to a short path distillation unit where 319 grams of the material were stripped at 270° C. and a residual pressure of 100 µm Hg, yielding 279 g of the final product having an acid number of 42 mg KOH/g and a viscosity of 360 cps. The product was characterized with color 1–2 on the Gardner scale, and had low odor typical for the soybean oil.

EXAMPLE 2

Example 1 was repeated except that safflower oil was substituted for soybean oil. The final product, having an acid number of 40 mg KOH/g, color 1–2 on the Gardner scale, and a viscosity of 420 cps, was recovered.

EXAMPLE 3

Example 1 was repeated except that sunflower oil was substituted for soybean oil. The final product, having an acid number of 41 mg KOH/g, color 1–2 on the Gardner scale, and a viscosity of 420 cps, was recovered.

EXAMPLE 4

Example 1 was repeated, except that 64 g mono(2-ethylhexyl)maleate was employed. The final product, having an acid number of 27 mg KOH/g, color 1–2 on the Gardner scale, and a viscosity of 320 cps, was recovered.

EXAMPLE 5

Example 1 was repeated, except that 127 g mono(2-ethylhexyl)maleate was employed. The final high load product, having an acid number of 58 mg KOH/g, color 2–3 on the Gardner scale, and a viscosity of 1300 cps, was recovered.

EXAMPLE 6

Example 1 was repeated, except that 85 g monobutyl maleate was substituted for 104 g mono(2-ethylhexyl) maleate. The final product, having an acid number of 46 mg KOH/g, color 1–2 on the Gardner scale, and a viscosity of 750 cps, was recovered.

EXAMPLE 7

Example 1 was repeated, except that 125 g mono (isocetyl)maleate was substituted for 104 g mono(2-ethylhexyl) maleate. The final product, having an acid number of 32 mg KOH/g, color 1–2 on the Gardner scale, and a viscosity of 820 cps, was recovered.

EXAMPLE 8

Example 1 was repeated, except that 156 g di(2-ethylhexyl)maleate was substituted for 104 g of the monoester. The final product, having an acid number of 0.4 mg KOH/g, color 1–2 on the Gardner scale, and a viscosity of 450 cps, was recovered.

EXAMPLE 9

Example 8 was repeated, except that 209 g of the diester was employed. The final product, having an acid number of 0.3 mg KOH/g, color 1–2 on the Gardner scale, and a viscosity of 615 cps, was recovered.

EXAMPLE 10

Example 1 was repeated, except that 48 g maleic acid was substituted for 104 g of mono(2-ethylhexyl) maleate. The final product, having an acid number of 76 mg KOH/g, color 3–4 on the Gardner scale, and a viscosity of 32,000 cps, was recovered.

EXAMPLE 11

Example 10 was repeated, except that 36 g of maleic acid was employed. The final product, having an acid number of 61 mg KOH/g, color 3–4 on the Gardner scale, and a viscosity of 5,600 cps, was recovered.

EXAMPLE 12

Example 10 was repeated, except that 24 g of maleic acid was employed. The final product, having an acid number of 41 mg KOH/g, color 2–3 on the Gardner scale, and a viscosity of 1,200 cps, was recovered.

EXAMPLE 13

Example 12 was repeated, except that 24 g of fumaric acid was substituted for maleic acid. The final product, having an acid number of 41 mg KOH/g, color 2–3 on the Gardner scale, and a viscosity of 1,200 cps, was recovered.

EXAMPLE 14

Example 1 was repeated, except that 300 g methyl linoleate was substituted for 329 g of soybean oil. Resulting product was a clear, straw colored liquid having an acid number of 46 mg KOH/g.

EXAMPLE 15

Example 1 was repeated, except that 300 g propylene glycol monolinoleate was substituted for 329 g of soybean oil. Resulting product was a clear, straw colored liquid having an acid number of 41 mg KOH/g.

EXAMPLE 16

Example 1 was repeated, except that 300 g glycerine dilinoleate was substituted for 329 g of soybean oil. Resulting product was a clear, straw colored liquid having an acid number of 44 mg KOH/g.

Surprisingly, the present ester adducts, having a higher molecular weight than their corresponding polyacid adducts, had a significantly reduced Brookfield viscosity which permits correspondingly higher loading in formulations. This unusual effect is illustrated in the following TABLE I where various concentrations of the maleated functionality were used and incorporated into soybean oil to form the corresponding adducts.

TABLE I

| Product Example | Maleated functionality Employed | % maleated linoleate incorporated in the oil | Visc. (cps) |
|---|---|---|---|
| 4 | mono(2-ethylhexyl) maleate | 40 | 320 |
| 1 | mono(2-ethylhexyl) maleate | 60 | 360 |
| 5 | mono(2-ethylhexyl) maleate | 75 | 1,300 |
| 8 | di(2-ethylhexyl) maleate | 60 | 450 |
| 9 | di(2-ethylhexyl) maleate | 80 | 615 |
| 12 | maleic acid | 32 | 1,200 |
| 10 | maleic acid | 64 | 32,000 |

The above experiments show that 75% incorporation of the ester adduct produced a viscosity of 1,300 cps; whereas only 32% (less than half) incorporation of the polyacid adduct produced a product of almost equal viscosity and 64% incorporation of the polyacid adduct produced a substantially unspreadable product having a viscosity of 32,000 cps.

Further comparative testing between the maleic diacid/soybean oil adduct and moderate and high load samples of mono(2-ethylhexyl) maleate/soybean oil adducts was carried out with the adducts alone and in a typical aqueous formulation consisting of 0.4% wt. % crosslinked methyl vinyl ether/maleic acid copolymer+5.0 wt. % glyceryl stearate (CERASYNT GMS)+2.0 wt. % polyethylene glycol (20) stearate+4.0 wt. % of the adduct+water (q.s.). The results of these tests applied to human skin are reported in following TABLE II.

TABLE II

| Adduct Alone | | | |
|---|---|---|---|
| Tack | Moderate | Low | Moderate |
| Feel (on Skin) | Heavy | Light/Drier | Heavy |
| Slip | Moderate | Moderate | Moderate |
| Odor | Typical | Light | Light |
| Adduct of Example | 12 | 1 | 5 |
| Adduct in Formula | | | |
| Tack | Moderate | Slight | Moderate |
| Afterfeel | Moderate Drag | Slight Drag | Slight Drag |
| Slip | Good | Good | Good |
| Rub-In | Good | Good | Good |
| Adduct of Example | 12 | 1 | 5 |

What is claimed is:

1. A moisturizing compound as an adduct for hair, skin, leather and vinyl cleaning and conditioning formulations having the formula

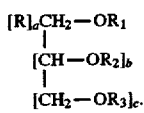

wherein
b and c are each independently 0 or 1;
a is zero when b and/or c has a positive value and a is one when b and c are zero;
R is hydrogen or $C_1$ to $C_{20}$ alkyl;
$R_1$, $R_2$ and $R_3$ are each independently —$COR_6$, or

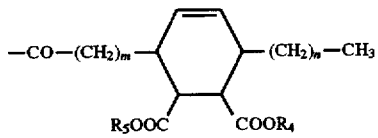

in which $R_6$ is $C_{10}$ to $C_{22}$ alkenyl or alkyl optionally substituted with hydroxy, m and n each have a value of from 3 to 9 with the proviso at least one of $R_1$, $R_2$ and $R_3$ in the adduct product is

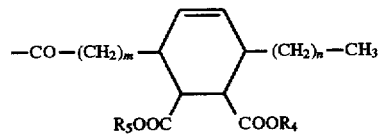

at least one of $R_4$ and $R_5$ is a $C_1$ to $C_{22}$ radical of alkyl, alkenyl or hydroxy alkyl and any other of $R_4$ or $R_5$ is hydrogen or $C_1$ to $C_{22}$ radical of alkyl, alkenyl or hydroxy alkyl.

2. The compound of claim 1 wherein the sum of m and n is 12.

3. The compound of claim 1 wherein b and c are each 1 and a is zero.

4. The compound of claim 1 wherein $R_1$ and $R_3$ are —$COR_6$.

5. The compound of claim 1 wherein one of $R_4$ and $R_5$ is $C_1$ to $C_{22}$ alkyl and the other is hydrogen.

6. The compound of claim 1 wherein $R_4$ and $R_5$ are each $C_1$ to $C_{22}$ alkyl.

7. The compound of claim 6 wherein at least one of $R_4$ and $R_5$ is 2-ethylhexyl.

8. The compound of claim 1 having a Brookfield viscosity of between about 100 and about 1,500 cps.

9. A process for the preparation of the ester adduct of claim 1 which comprises effecting a Dieis-Alder condensation reaction between a conjugated polyolefinic oil containing the functional group —CH=CH—$(CH_2)_p$—(CH=CH)$_q$—$(CH_2)_r$—CH=CH— where p and r each independently have a valve of 0 to 3 and q has a value of 0 or 1 and a coreactant ester having the formula $R_4$OOC—CH=CH—COOR$_5$ wherein $R_4$ and $R_5$ are as defined, at a temperature of from about 150° C. to about 260° C.

10. The process of claim 9 wherein p and r are zero and q is zero and the mole ratio of —CH=CH—CH=CH— radical to ester coreactant is between about 1:1 and about 3:1.

11. The process of claim 9 wherein the polyolefinic oil is a vegetable oil.

12. The process of claim 11 wherein said vegetable oil is selected from the group consisting of soybean oil, safflower oil, sunflower oil and cottonseed oil.

13. The process of claim 9 wherein said ester coreactant is selected from the group consisting of ethyl hexyl maleate, butyl maleate, and isocetyl maleate.

14. The process of claim 13 wherein said ester is coreactant ethyl hexyl maleate.

* * * * *